(12) United States Patent
Lait et al.

(10) Patent No.: US 11,850,265 B2
(45) Date of Patent: Dec. 26, 2023

(54) TREATMENT AND PROPHYLAXIS OF RADIATION DERMATITIS

(71) Applicant: RADIADERM LIMITED, London (GB)

(72) Inventors: Mark Lait, Hertford (GB); George Bishop, Carlstadt, NJ (US)

(73) Assignee: RADIADERM LIMITED, London (GB)

( * ) Notice: Subject to any disclaimer, the term of this patent is extended or adjusted under 35 U.S.C. 154(b) by 442 days.

(21) Appl. No.: 17/033,294

(22) Filed: Sep. 25, 2020

(65) Prior Publication Data
US 2021/0008116 A1 Jan. 14, 2021

Related U.S. Application Data

(60) Continuation of application No. 15/988,159, filed on May 24, 2018, now abandoned, which is a division of application No. 14/772,139, filed as application No. PCT/EP2014/054319 on Mar. 6, 2014, now Pat. No. 10,098,912.

(60) Provisional application No. 61/773,225, filed on Mar. 6, 2013.

(30) Foreign Application Priority Data

Mar. 6, 2013 (GB) ...................................... 1304041

(51) Int. Cl.
| | |
|---|---|
| A61K 35/20 | (2006.01) |
| A61K 9/06 | (2006.01) |
| A61K 9/00 | (2006.01) |
| A61K 47/10 | (2017.01) |
| A61K 47/14 | (2017.01) |
| A61K 47/18 | (2017.01) |
| A61K 47/32 | (2006.01) |
| A61K 47/36 | (2006.01) |
| A61K 47/46 | (2006.01) |
| A61K 31/047 | (2006.01) |
| A61K 31/12 | (2006.01) |
| A61K 31/133 | (2006.01) |
| A61K 31/216 | (2006.01) |
| A61K 31/275 | (2006.01) |
| A61K 38/01 | (2006.01) |

(52) U.S. Cl.
CPC ............ *A61K 35/20* (2013.01); *A61K 9/0009* (2013.01); *A61K 9/0014* (2013.01); *A61K 9/06* (2013.01); *A61K 31/047* (2013.01); *A61K 31/12* (2013.01); *A61K 31/133* (2013.01); *A61K 31/216* (2013.01); *A61K 31/275* (2013.01); *A61K 38/018* (2013.01); *A61K 47/10* (2013.01); *A61K 47/14* (2013.01); *A61K 47/18* (2013.01); *A61K 47/32* (2013.01); *A61K 47/36* (2013.01); *A61K 47/46* (2013.01)

(58) Field of Classification Search
CPC ..................................................... A61K 35/20
See application file for complete search history.

(56) References Cited

U.S. PATENT DOCUMENTS

| | | | |
|---|---|---|---|
| 5,736,128 | A | 4/1998 | Chaudhuri et al. |
| 6,255,290 | B1 | 7/2001 | von Borstel et al. |
| 9,345,720 | B2 | 5/2016 | Hensby et al. |
| 2005/0175559 | A1 | 8/2005 | DiNardo et al. |
| 2005/0238610 | A1 | 10/2005 | Nielsen et al. |
| 2007/0079446 | A1 | 4/2007 | Lupia et al. |
| 2007/0248555 | A1 | 10/2007 | Watson |
| 2009/0104129 | A1 | 4/2009 | Chen et al. |
| 2011/0217249 | A1 | 9/2011 | Dreher |
| 2011/0280943 | A1 | 11/2011 | Mansouri et al. |
| 2011/0300085 | A1 | 12/2011 | Courbon et al. |
| 2012/0164096 | A1 | 6/2012 | Prieto Alonso |
| 2012/0171308 | A1 | 7/2012 | Da Luz Moreira et al. |
| 2012/0177588 | A1 | 7/2012 | Desmurs et al. |
| 2013/0209378 | A1 | 8/2013 | Harris et al. |

FOREIGN PATENT DOCUMENTS

| | | |
|---|---|---|
| CN | 101505781 A | 8/2009 |
| KR | 1020040031815 A | 4/2004 |
| WO | 9707779 A2 | 3/1997 |
| WO | 2006105661 A1 | 10/2006 |
| WO | WO2006105661 * | 10/2006 |
| WO | 2007150049 A2 | 12/2007 |

OTHER PUBLICATIONS

Prweb. Water-Jel Technologies Launches New Lactokine-Based Skincare System for Radiation Patients. January (Year: 2011).*
Digit-Eyes. Radiaderm Radiation Releif System R1/R2. Retrieved online Feb. (Year: 2023).*
Seasame. What is Deionized Water in Your Skin Care Products? (Year: 2012), 3 pages.
European Search Report in corresponding European Application No. 14714943.9 dated Aug. 26, 2016, 4 pages.
Hafner et al. Prophylaxis of Acute Radiation Dermatitis with an Innovative FDA-approved two step skin care system in a patient with head and neck cancer undergoing a platin-based radiochemotherapy: a case report and review of the literature: 2013 Dermatology (Basel, Switzerland) 2013, vol. 227m NR. 2, pp. 171-174.
Canadian Office Action dated Jun. 12, 2019 (Jun. 12, 2019), for Canadian Patent Application No. 2,903,647, 4 pages.
Water-Jel: "New Advanced Skin Defense During and After Radiotherapy", 2016, 8 pages.

(Continued)

*Primary Examiner* — Sarah Alawadi
(74) *Attorney, Agent, or Firm* — Richard A. Fagin

(57) ABSTRACT

The present invention relates to topical formulations comprising purified water, milk protein fluid and thickener, in particular a hydrogel and a lotion, and their use in treatment, in particular in a two-step process for the treatment of radiation dermatitis.

17 Claims, No Drawings

(56) References Cited

OTHER PUBLICATIONS

Water-Jel, Water-Technologies Lauches New Lactokin-Based Skincare System for Radiation Patients, Oct. 14, 2010 (Oct. 14, 2010), 3 pages.
International Preliminary Report on Patentability in corresponding PCT Application No. PCT/EP2014/054319, dated Sep. 8, 2015, 7 pages.
International Search Report and Written Opinion in corresponding PCT Application No. PCT/EP2014/054319, dated May 21, 2014, 10 pages.

* cited by examiner

TREATMENT AND PROPHYLAXIS OF RADIATION DERMATITIS

This application is a continuation application of U.S. patent application Ser. No. 15/988,159 filed May 24, 2018, which is a divisional application of U.S. patent application Ser. No. 14/772,139 filed Sep. 2, 2015, which was a U.S. National Phase Application under 35 U.S.C. § 371 of International Patent Application No. PCT/EP2014/054319, filed Mar. 6, 2014, and claims the benefit of priority under 35 U.S.C Section 119(e) of U.S. Application Ser. No. 61/773,225 filed Mar. 6, 2013; Great Britain Application No. 1304041.5, filed Mar. 6, 2013, all of which are incorporated by reference in their entireties.

The present invention relates to topical formulations comprising purified water, milk protein fluid and thickener, in particular a hydrogel and a lotion, and their use in treatment, in particular in a two-step process for the treatment of radiation dermatitis.

BACKGROUND

A radiation burn is damage to the skin or other biological tissue caused by exposure to radiation. The radiation types of greatest concern are thermal radiation, radio frequency energy, ultraviolet light and ionising radiation.

Radiation therapy or radiotherapy is the medical use of ionising radiation, generally as part of cancer treatment to control or kill malignant cells. Radiation therapy may be curative in a number of types of cancer if the cancer cells are localised to one area of the body. It may also be used as part of curative therapy, to prevent tumour recurrence after surgery to remove a primary malignant tumour (for example, early stages of breast cancer). Radiation therapy is synergistic with chemotherapy, and has been used before, during and after chemotherapy in susceptible cancers.

Radiation therapy has several applications in non-malignant conditions, such as the treatment of trigeminal neuralgia, acoustic neuromas, severe thyroid eye disease, pterygium, pigmented villonodular synovitis and prevention of keloid scar growth, vascular restenosis, and heterotopic ossification. However, its use in non-malignant conditions is limited, partly by worries about the risk of radiation-induced cancers.

Radiation dermatitis or radiodermatitis is a skin disease associated with exposure to ionising radiation. Radiation dermatitis occurs to some degree in most patients receiving radiation therapy, with or without chemotherapy. As many as 95% of patients treated with radiation therapy for cancer will experience a skin reaction. Some reactions are immediate, while others may be later (e.g. months after treatment) (Porock et al 2009). Radiation dermatitis generally manifests within a few weeks after the start of radiotherapy, while typically presenting as red patches (erythema). It may also present with desquamation or blistering.

The reaction may become more severe during the treatment and for up to about one week following the end of radiation therapy. The skin may ultimately thin and begin to weep because of loss of integrity of the epithelial barrier and decreased oncotic pressure referred to as desquamation. Whilst this phase is uncomfortable, recovery is usually quick. Skin reactions tend to be worse in areas where there are natural folds in the skin, such as underneath the female breast, behind the ear and in the groin. Over time, the irritated skin will heal, but may not be as elastic as it was before.

Radiodermatitis can be painful and embarrassing and has been associated with decreased quality of life (Fisher et al 2000). The appearance and development of radiation dermatitis depends on many factors including the applied dose of radiation, type of radiation, energy level of the dose, total period of treatment, size of area treated, fractionation and factors that vary from individual to individual. Severe radiodermatitis necessitates treatment modifications or delays, which may compromise the efficacy of radiotherapy (Hymes et al 2006).

Given the scope and severity of radiodermatitis, it is crucial that oncology nurses are familiar with the clinical presentation and evidenced-based interventions for radiodermatitis.

However, an investigative survey by D'haese et al (2005) found that there is wide discrepancy between nursing interventions for the prevention and management of radiodermatitis. D'haese interviewed radiation oncology nurses in Belgium and found only a small to moderate level of agreement between nurses regarding the prevention and management of radiodermatitis. The greatest variation was between preventative practices. These results suggest that there is confusion among oncology nurses (and likely their patients) regarding the prevention and management of radiodermatitis.

Numerous treatments have been suggested for the prevention and management of radiodermatitis. Among the suggested treatments are: ascorbic acid, vitamin D, aloe vera gel, chamomile and calendula creams and almond ointment (Kassab et al 2009), moisturisation with a non-scented, hydrophilic, lanolin-free cream, topical steroids, washing gently with a mild soap or shampoo (Bolderston et al 2006). Gentle washing has been found to be more effective in the prevention and treatment of radiodermatitis than topical aloe vera (Richardson et al 2005).

However, there is very little scientific support for any of these treatments. Thus there is a need for a topical formulation that is effective both in prophylaxis and treatment of radiation dermatitis and is simple to use.

At the present time the standard of care for radiation dermatitis is a clean dry dressing. However, this approach does not provide soothing or actively assist the healing of the damaged area.

Here we present a novel topical formulation for the prophylaxis and treatment of radiation dermatitis that has been shown to reduce the likelihood of developing grade 3 or 4 radiation dermatitis (on the RTOG or NCI scales). Furthermore, the treatment is easy to use by the patient.

SUMMARY OF INVENTION

Thus there is provided a topical formulation for the prophylaxis and or treatment of radiation dermatitis comprising purified water, milk protein fluid and a thickener.

It appears that milk protein fluid has advantageous properties for the prophylaxis or treatment of radiation dermatitis.

Advantageously, a formulation comprising purified water, thickener and milk protein fluid can be modified to provide various thicknesses of topical treatment. For example, a thick viscous formulation to sit on the skin following treatment with radiation will absorb heat whilst permitting application to a discrete area. Furthermore, the milk protein fluid can be applied to the area of radiation without being wasted on "non-damaged" areas. Alternatively for example, a less viscous formulation that can be more readily absorbed by the skin to provide ongoing moisture and skin conditioning in the period following treatment.

In one embodiment there is provided a hydrogel formulation for primary treatment of the radiation dermatitis, in particular for re-hydrating and soothing the affected skin.

Primary treatment as employed herein means treatment immediately following or shortly after radiation treatment, for example within 12 hours of radiation treatment, such as within 11, 9, 8, 7, 6, 5, 4, 3, 2 or 1 hour or less, particularly within 2 hours.

In one embodiment there is provided a lotion for moisturising and maintaining the integrity of the affected skin.

In a further aspect of the invention there is provided a two-step process for the prophylaxis and/or treatment of radiation dermatitis comprising the steps:
   a) applying a layer of the hydrogel of the invention to unbroken skin following radiation therapy and leaving it on the skin for at least 20 minutes;
   b) applying the lotion of the invention to unbroken skin to provide moisturisation.

In a further aspect of the invention there is provided a two-step process for the prophylaxis and/or treatment of radiation dermatitis comprising the steps:
   c) applying a layer of the hydrogel of the invention to unbroken skin following radiation therapy and leaving it on the skin for at least 20 minutes;
   d) applying the lotion of the invention to unbroken skin to provide moisturisation; wherein step b) is repeated as often as desired to relieve discomfort.

In one embodiment the layer of hydrogel applied in step a) is a generous layer, such as 0.5 mm or more.

In a further aspect of the invention there is provided a kit of parts comprising at least one application of the hydrogel formulation and at least one application of the lotion formulation.

In a yet further aspect of the invention there is provided a method of prophylaxis and/or treatment for radiation dermatitis comprising administering to patient in need thereof a hydrogel of the invention and/or a lotion of the invention.

The present disclosure for the first time provides a specialised and safe formulation for soothing and promoting healing and regeneration of damaged tissue.

DESCRIPTION

Topical formulation as employed herein means preparation that is applied to the surface of the body, such as the skin, including but not limited to a cream, foam, ointment, paste, lotion or gel, including a hydrogel.

Prophylaxis as employed herein refers to the prevention of condition aimed at stopping the condition developing, such as radiation dermatitis.

Treatment as employed herein refers to the reversal of a condition, amelioration or relief of symptoms associated with a condition or prevention of further development/worsening of a condition, such as radiation dermatitis.

Radiation includes thermal radiation, radio frequency energy, ultraviolet light and ionising radiation, particularly ionising radiation.

Radiation dermatitis as employed herein is not intended to mean or include sunburn.

In one embodiment radiation means ionising radiation.

Radiation dermatitis as employed herein refers to the skin disease associated with exposure to ionising radiation. Grades of radiation are described by the RTOG and NCI scales described below.

Purified water as employed herein means water that has been cleaned and/or filtered to be suitable for topical application. As employed herein, purified water has a heat-absorbing function, aimed at cooling the sensation of heat in the skin following exposure to radiation. The purified water also acts as a solvent.

Milk protein fluid or milk protein as defined herein is the INCI name for LACTOKINE fluid and refers to a complex comprising one or more water-soluble milk proteins, for example caseins and/or whey proteins and one or more cytokines, such as LACTOKINE, more specifically LACTOKINE fluid PF.

LACTOKINE fluid contains a network of activated and stabilised signal molecules derived from milk, which stimulates the skin's own protection system. When employed in formulations of the present disclosure it is thought to have regenerative and anti-inflammatory properties. Typically LACTOKINE fluid has a pH range of 5.8-7.0.

LACTOKINE fluid is prepared from milk, which contains a variety of nutrients such as protein, milk fat and vitamins A, D, E, B2 and B12, folic acid and calcium. LACTOKINE fluid is designed to stimulate the skin's regenerative cell functions by increasing energy levels of the cells and counteracting formation of inflammatory mediator prostaglandin E2 (PGE2).

In one embodiment the milk protein fluid is added to the formulation in dried form and rehydrated in the aqueous environment of the formulation.

In one embodiment the formulation comprises milk protein fluid, such as 2-8% milk protein fluid. Such as 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8 or 7.9% milk protein fluid, for example LACTOKINE fluid, such as 4-8% LACTOKINE fluid, such as 5% LACTOKINE fluid.

LACTOKINE fluid is available from CLR Chemisches Laboratorium, Berlin.

Thickener or thickening agent as employed herein is an ingredient or ingredients that increase the viscosity of a formulation without substantially altering its other properties. Examples of thickening agents include polysaccharides such as starches, in particular corn starch, poly(acrylic acids), gelling agents and acrylates such as acrylates/$C_{10-30}$ alkyl acrylate crosspolymer.

The formulations and methods of the present disclosure when employed help maintain skin integrity, minimise the deleterious effects of radiation treatment and reduce opportunistic infections that may occur when skin is damaged.

In one embodiment there is provided a topical formulation with a viscosity in the range 25,000 to 130,000 cP or in the range 290,000 to 510,000 cP.

In one embodiment the topical formulation according to the present disclosure is a hydrogel formulation. Hydrogel formulation as employed herein refers to a formulation capable of absorbing water and swelling. The hydrogel generally is a gel formed of a network of hydrophilic polymer chains capable of containing up to 99.9% water, for example polyacrylamide or polyethylene oxide. Hydrogels are typically highly flexible and maintain the moisture around the wound to prevent it drying out and shrinking. The maintenance of moisture around the wound may also minimise scarring and prevent reduced flexibility in the area of skin damage. This is advantageous because it may reduce pain associated with scar tissue and avoids skin thickening and reduced skin elasticity which, in skin folds, can be problematic.

It is desirable to avoid skin toughness that can arise following damage to the skin because toughened skin is prone to flaking and cracking which in turn can lead to inflammation and infection.

In one embodiment the hydrogel formulation has a viscosity in the range 290,000 to 510,000 cP such as 300,000 to 500,000 cP.

In one embodiment the hydrogel formulation has a viscosity in the range 300,000 to 360,000 cP measure using spindle #64 spindle (with guard) @ 1 RPM. For example 330,000 cP.

In one embodiment the hydrogel formulation has a viscosity in the range 70,000 to 200,000. Such as 70,000 to 200,000 cP measured using spindle #64 @ 1.5 RPM.

In one embodiment the topical formulation according to the present disclosure is a lotion. Lotion as employed herein refers to a liquid topical formulation suitable for spreading.

Spreading as employed herein refers to the ability of the formulation to be distributed over the surface of the skin, in particular as a thin layer.

Thin layer as employed herein is generally 1 mm or less, for example 0.5 mm or less, such as 0.3 mm or less in depth measured from the skin surface.

In one embodiment a lotion has a viscosity in the range 25,000 to 130,000 cP such as 30,000 to 120,000 cP.

In one embodiment the lotion has a viscosity in the range 40,000 to 75,000 cP. Such as 40,000 to 75,000 cP measured using spindle #64 @ 1.5 RPM.

In one embodiment the lotion has a viscosity in the range 30,000 to 50,000 cP. Such as 30,000 to 50,000 cP measured using spindle #64 @ 5 RPM.

Viscosity as employed herein is a measure of a fluid's resistance to flow. It corresponds to a notional "thickness" of a liquid and is measured in cP (centipoise). Centipoise is a measure of viscosity on the CGS (centimetre gram second) scale. Water has a viscosity of 1 cP at 20° C. Viscosity can be measured using a Brookfield viscometer, such as a Brookfield DV II Pro. Generally viscosity is measured at room temperature, such as 20 to 25° C., preferably 25° C.

Preservative as employed herein refers to a substance that prevents decomposition or contamination either by microorganisms or by chemical change. Typical preservatives suitable for topical formulations include, but are not limited to, phenoxyethanol, ethylhexylglycerine, caprylyl glycol, chlorphenesin, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, other examples include, esters of parahydroxybenzoic acid; and other anti-microbial agents such as chlorhexidine, chlorocresol, benzoic acid and polymyxin.

In one embodiment the formulation comprises phenoxyethanol and ethylhexylglycerine such as Euxyl PE 9010.

In one embodiment the formulation comprises Mikrokill COS, INCI name phenoxyethanol and caprylyl glycol and chlorphenesin.

In one embodiment the formulation comprises preservative, for example 0.5-1.5% preservative, such as 0.55, 0.6, 0.65, 0.7, 0.75, 0.8, 0.85, 0.9, 0.95, 1.0, 1.05, 1.1, 1.15, 1.2, 1.25, 1.3, 1.35, 1.4 or 1.45% preservative, for example phenoxyethanol and/or ethylhexylglycerine, such as 0.75-1% phenoxyethanol and/or ethylhexylglycerine, in particular 0.75% or 1% phenoxyethanol and/or ethylhexylglycerine. Or for example phenoxyethanol and caprylyl glycol and chlorphenesin, such as 1% phenoxyethanol and caprylyl glycol and chlorphenesin In one embodiment the topical formulation comprises a chelating agent, for example 0-1% chelating agent, such as 0.05, 0.1, 0.15, 0.2, 0.25, 0.3, 0.35, 0.4, 0.45, 0.5, 0.55, 0.6, 0.65, 0.7, 0.75, 0.8, 0.85, 0.9 or 0.95% chelating agent, in particular edetate disodium. In one embodiment the formulation comprises 0.05-0.2% edetate disodium. In one embodiment the hydrogel comprises 0.1% edetate disodium. In one embodiment the lotion comprises 0.05 or 0.2% edetate disodium.

Chelating agent as employed herein is a substance that forms soluble, complex molecules with certain metal ions, inactivating the ions so that they cannot normally react with other elements or ions to produce precipitates or scale, for example, edetate disodium or EDTA.

In one embodiment the hydrogel comprises purified water, for example 89-93.5% water, such as 89.5, 90, 90.5, 91, 91.5, 92, 92.5 or 93% water. In one embodiment the hydrogel formulation comprises 91.15% water.

In one embodiment the balance of the hydrogel is made up of water.

In one embodiment the hydrogel comprises preservative, for example 0.5-1.2% preservative, such as 0.55, 0.6, 0.65, 0.7, 0.75, 0.8, 0.85, 0.9, 0.95, 1.0, 1.05, 1.1 or 1.15% preservative such as phenoxyethanol and ethylhexylglycerine. In one embodiment the formulation comprises 0.75% phenoxyethanol and ethylhexylglycerine.

In one embodiment the hydrogel comprises a chelating agent. Such as 0-1% chelating agent, such as 0.05, 0.1, 0.15, 0.2, 0.25, 0.3, 0.35, 0.4, 0.45, 0.5, 0.55, 0.6, 0.65, 0.7, 0.75, 0.8, 0.85, 0.9 or 0.95% chelating agent, such as edetate disodium. Preferably 0.1% edetate disodium.

In one embodiment the hydrogel further comprises one or more ingredients independently selected from: poly(acrylic acid), pH modifier and moisturising agent.

Poly(acrylic acid)r as employed herein means a series of polymers of acrylic acid. Poly(acrylic acids) function as both a thickener and an emulsion stabiliser. Suitable poly (acrylic acids) include, but are not limited to, poly(acrylic acid) 940 and poly(acrylic acid) TR1.

In one embodiment the hydrogel comprises carbomer, for example 0.1-0.9% poly(acrylic acid), that is 0.1-0.9% of the total formulation is carbomer, such as 0.2, 0.3, 0.4, 0.5, 0.6, 0.7 or 0.8%. In one embodiment the formulation comprises 0.7% poly(acrylic acid), such as poly(acrylic acid) 940 and poly(acrylic acid) TR1, in particular 0.4% poly(acrylic acid) 940 and 0.3% poly(acrylic acid) TR1.

pH modifier as employed herein is a neutralising agent, including those suitable for neutralising carbomers, such as inorganic bases or triethanolamine/trolamine.

In one embodiment the hydrogel comprises pH modifier, for example 0.1-3.5% pH modifier, such as 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3 or 3.4% such as triethanolamine. Preferably 0.8% triethanolamine.

Moisturising agent as employed herein means an agent designed to make the skin softer and more pliable and increase skin hydration. Suitable moisturisers include, but are not limited to, glycerine, sorbitol, polyethylene glycols, urea, and propylene glycol, such as glycerine.

Advantageously, moisturising agents in the formulation help maintain moisture in the skin, thereby helping prevent skin dryness, flaking and cracking. This in turn helps prevent the skin becoming painful and helps prevent opportunistic infections that may occur in cracked or damaged skin.

In one embodiment the hydrogel comprises moisturising agent. Such as 0.5-1.15% moisturising agent, for example 0.6, 0.7, 0.8, 0.9, 1.0 or 1.1% moisturising agent, such a glycerine, in particular 1% glycerine.

In one embodiment the hydrogel comprises thickener, for example 0.25-0.85% thickener, such as 0.3, 0.35, 0.4, 0.45, 0.5, 0.55, 0.6, 0.65, 0.7, 0.75 or 0.8% thickener, such as acrylates/$C_{10-30}$ alkyl acrylate crosspolymer. Preferably 0.5% acrylates/$C_{10-30}$ alkyl acrylate crosspolymer.

In one embodiment there is provided a hydrogel comprising one or more ingredients selected from: poly(acrylic acid) such as poly(acrylic acid) 940 and/or poly(acrylic acid) TR1, pH modifier such as trolamine, and moisturising agent such a glycerine.

In one embodiment there is provided hydrogel consisting essentially of 89-93.5% purified water, 4-8% milk protein fluid, 0.5-1.15% glycerine, 0.1-3.5% trolamine, 0.5-1.2% preservative, 0.1-0.9% poly(acrylic acid), 0.25-0.85% thickener, and 0-1% edetate disodium.

In one embodiment there is provided a hydrogel according to the invention wherein the thickener is acrylate/$C_{10-30}$ alkyl acrylate crosspolymer.

Acrylates/$C_{10-30}$ alkyl acrylate crosspolymer is a cross-linked polyacrylic acid.

In one embodiment there is provided a hydrogel consisting essentially of 91.15% purified water, 5% LACTOKINE fluid, 1% glycerine, 0.8% trolamine, 0.75% phenoxyethanol and ethylhexylglycerine, 0.4% poly(acrylic acid) 940, 0.3% poly(acrylic acid) TR1, 0.5% acrylate/C.sub.10-30 alkyl acrylate crosspolymer, and 0.1% edetate disodium. In one embodiment the viscosity is in the range 290,000 to 510,000 cP, for example 300,000 to 500,000, preferably 300,000 to 350,000.

In one embodiment the hydrogel has a high thermal capacity. Whilst not wishing to be bound by theory, this is believed to be due to the high water content of the hydrogel. In use, some of the moisture penetrates into the skin, creating a thermal convective effect to transfer heat caused by the radiation treatment, from the inner skin layers to the surface. Evaporative cooling then takes place. The net result is increased skin hydration coupled with lowered subcutaneous skin temperatures.

Thermal capacity as employed herein means the amount of heat required to raise the temperature of the gel by 1° C.

In one embodiment the high thermal capacity of the hydrogel functions to absorb heat from the skin thereby providing a cooling sensation.

The high water content of the hydrogel enables it to absorb heat from the skin. Whilst not wishing to be bound by theory, the present inventors believe that this helps prevent the development of radiation burn by reducing the layers of skin cells permeated by the heat associated with radiation therapy. This is analogous with treatment of heat burns with water or a water-based gel.

In one embodiment the topical formulation is a lotion.

Lotion as employed herein means a low to medium viscosity topical formulation for application to unbroken skin. By contrast, creams and gels, including hydrogels, have a higher viscosity.

Advantageously, a lower viscosity means that the lotion is more easily absorbed by the skin and is easier to spread on the skin because it is less likely to drag the skin surface. This can be particularly useful where the patient is suffering pain or loss of skin integrity at the treatment site.

In one embodiment the lotion comprises purified water, such as 54.5-80% water. Such as 55, 55.5, 56, 56.5, 57, 57.5, 58, 58.5, 59, 59.5, 60, 60.5, 61, 61.5, 62, 62.5, 63, 63.5, 64, 64.5, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79 or 79.5% water. Preferably 54.5-65.5% or 70-80% water, most preferably 58.8% or 75.95% water.

In one embodiment the balance of the lotion is water.

In one embodiment the lotion comprises preservative, such as 0.5-1.5% preservative. Such as 0.55, 0.6, 0.65, 0.7, 0.75, 0.8, 0.85, 0.9, 0.95, 1.0, 1.05, 1.1, 1.15, 1.2, 1.25, 1.3, 1.35, 1.4 or 1.45% preservative such as phenoxyethanol and ethylhexylglycerine or phenoxyethanol and caprylyl glycol and chlorphenesin. Preferably 1% phenoxyethanol and ethylhexylglycerine or 1% phenoxyethanol and caprylyl glycol and chlorphenesin.

In one embodiment the preservative employed in the formulation is Mikrokill COS.

In one embodiment the preservative employed in the formulation is Euxyl PE 2010.

In one embodiment the lotion comprises a chelating agent. Such as 0-1% chelating agent, such as 0.05, 0.1, 0.15, 0.2, 0.25, 0.3, 0.35, 0.4, 0.45, 0.5, 0.55, 0.6, 0.65, 0.7, 0.75, 0.8, 0.85, 0.9 or 0.95% chelating agent, such as edetate disodium. Preferably 0.2% or 0.05% edetate disodium.

In one embodiment the edetate disodium employed in the formulation is Versene NA.

In one embodiment the lotion further comprises one or more ingredients independently selected from non-metallic UVA and/or UVB inhibitor, $C_{12-15}$ alkyl benzoate, caprylyl methicone, emulsifier, gelling agent, glyceryl monostearate, glyceryl stearate citrate, allantoin, caprylic triglyceride, dimethicone, solvent, mineral oil, pH modifier, chelating agent, preservative and buffer.

UVA inhibitor as employed herein means a substance capable of blocking or absorbing ultraviolet waves in the UVA spectrum with a wavelength of 320-400 nm. Particularly UVA absorbers such as avobenzone and octoxinate.

UVB inhibitor as employed herein means a substance capable of blocking or absorbing ultraviolet waves in the UVB spectrum with a wavelength of 290-320 nm. Particularly UVB absorbers such a octocrylene, homosalate and octoxinate.

In one embodiment the lotion comprises non-metallic UVA and/or UVB inhibitor such as 7-19% inhibitor. Such as 8, 9, 10, 11, 12, 13, 14, 15, 16, 17 or 18% inhibitor, such as 16% inhibitor.

In one embodiment the non-metallic UVA and/or UVB inhibitor is selected from octocrylene, octoxinate, avobenzone and homosalate or a mixture thereof. Preferably a mixture of octocrylene, octoxinate and avobenzone that total 16% of the total lotion. Preferably 10% octocrylene, 3% octoxinate and 3% avobenzone.

In one embodiment the octocrylene employed in the formulation is Neo Heliopan 303.

In one embodiment the octoxinate employed in the formulation is Neo Heliopan AV.

In one embodiment the avobenzone employed in the formulation is Neo Heliopan 357.

Mixture as employed herein means a combination of two or more ingredients selected from a list.

In one embodiment the lotion prevents further radiation damage by absorbing UV radiation.

Advantageously, preventing further radiation damage can lead to a better prognosis for the patient, including a shorter recovery time. It is important to protect the damaged area from further radiation exposure to give the skin time to heal.

$C_{12-15}$ alkyl benzoate as employed herein is an emollient, skin feel modifier, an anti-tackiness agent, lubricant, binder and wetting agent which also works as a solvent for sunscreen ingredients. It is a member of a class of ingredients known generically as skin conditioning agents.

In one embodiment the lotion comprises $C_{12-15}$ alkyl benzoate, such as 6-15% $C_{12-15}$ alkyl benzoate. Such as 7, 8, 9, 10, 11, 12, 13 or 14% $C_{12-15}$ alkyl benzoate. Preferably 8% $C_{12-15}$ alkyl benzoate.

In one embodiment the $C_{12-15}$ alkyl benzoate employed in the formulation is Surfest TN.

Skin conditioning agent as employed herein is a generic term encompassing emollients, humectants, occlusives and other miscellaneous ingredients including proteins, silicones, cationic surfactants and polymers that act on the surface of the skin to help it feel soft, smooth and pliable. Examples of suitable skin conditioning agents include, but are not limited to, $C_{12-15}$ alkyl benzoate, caprylyl methicone, glyceryl monostearate such as glyceryl stearate SE and glyceryl stearate, glyceryl stearate citrate, allantoin, caprylic triglyceride and dimethicone.

Smooth, pliable skin is beneficial because it is less prone to further damage, for example by snagging or cracking.

Caprylyl methicone as employed herein is a silicone based skin conditioning agent.

In one embodiment the lotion comprises caprylyl methicone, such as 1-5% caprylyl methicone. Such as 1.5, 2, 2.5, 3, 3.5, 4 or 4.5% caprylyl methicone.

In one embodiment the caprylyl methicone employed in the formulation is Silcare Silicone 41MI5.

In one embodiment the lotion comprises skin conditioning agent, for example 0.1-1.5% skin conditioning agent, such as 0.2, 0.3, 0.4, 0.5, 0.6, 0.7, 0.8, 0.9, 1.0, 1.1, 1.2, 1.3 or 1.4% skin conditioning agent. For example allantoin, preferably 0.5% allantoin.

Allantoin as employed herein refers to a chemical compound with formula $C_4H_6N_4O_3$. It is also called 5-ureidohydantoin or glyoxyldiureide. It is believed to function in increasing the smoothness of the skin; promoting cell proliferation and wound healing; and a soothing, anti-irritant, and skin protectant effect by forming complexes with irritant and sensitising agents.

In one embodiment the lotion comprises 2-6% skin conditioning agent such as 2.5, 3.0, 3.5, 4.0, 4.5, 5.0 or 5.5% skin conditioning agent. For example caprylic triglyceride, preferably 4% caprylic triglyceride.

Caprylic triglyceride as employed herein is a product derived from coconut oil and glycerin. It is considered an excellent emollient and skin-repairing ingredient in cosmetics due to its mix of fatty acids that skin can utilise to repair its surface and resist moisture loss. Caprylic/capric triglyceride can also function as a thickener, but its chief job is to moisturise and replenish skin.

In one embodiment the caprylic triglyceride employed in the formulation is Liponate GC.

In one embodiment the lotion comprises 1-3% dimethicone such as 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9% dimethicone. Preferably 2% dimethicone Dimethicone as employed herein, also known as polydimethylsiloxane (PDMS), is a silicone oil with many industrial applications. It is optically clear and generally inert, non-toxic, and non-flammable.

In one embodiment the dimethicone employed in the formulation is DC Q7-9120 silicone fluid.

In one embodiment the lotion comprises 2-6% mineral oil such as 2.5, 3.0, 3.5, 4.0, 4.5, 5.0 or 5.5% mineral oil, preferably 4% mineral oil.

Mineral oil as employed herein is any one of various colourless, odourless, light mixtures of alkanes in the $C_{15}$ to $C_{40}$ range from a non-vegetable (mineral) source, particularly a distillate of petroleum.

In one embodiment the mineral oil employed in the formulation is Drakeol 7.

As employed herein, the mineral oil in a dual role, as a skin protectant and a moisturiser.

Emulsifier as employed herein is a substance that enables two or more normally immiscible liquids to be mixed, that is, emulsified. Suitable emulsifiers include, but are not limited to, ceteareth-20 and cetearyl alcohol, such as surfawax SE; glyceryl monostearate such as glyceryl stearate SE and glyceryl stearate; glyceryl stearate citrate; glyceryl stearate and PEG-100 for example Arlacel 165-PW-(AP).

In one embodiment the lotion comprises emulsifier, such as 1-2.5% emulsifier. Such as 1.1, 1.2, 1.3, 1.4, 1.5, 1.6, 1.7, 1.8, 1.9, 2.0, 2.1, 2.2, 2.3 or 2.4% emulsifier, such as ceteareth-20 and cetearyl alcohol. Preferably 1% or 2% ceteareth-20 and cetearyl alcohol.

In one embodiment the ceteareth-20 and cetearyl alcohol employed in the formulation is Surfawax SE.

In one embodiment the ceteareth-20 and cetearyl alcohol employed in the formulation is Lipowax D.

In one embodiment the lotion comprises 1-2.5% emulsifier/thickener, such as 1.1, 1.2, 1.3, 1.4, 1.5, 1.6, 1.7, 1.8, 1.9, 2.0, 2.1, 2.2, 2.3 or 2.4% emulsifier/thickener. For example glyceryl stearate and PEG-100), preferably 1.5% glyceryl stearate and PEG-100.

In one embodiment the glyceryl stearate and PEG-100 employed in the formulation is Arlacel 165-PW-(AP).

In one embodiment the lotion comprises glyceryl monostearate, such as 1-2.5% glyceryl monostearate. Such as 1.1, 1.2, 1.3, 1.4, 1.5, 1.6, 1.7, 1.8, 1.9, 2.0, 2.1, 2.2, 2.3 or 2.4% glyceryl monostearate, such as glyceryl stearate SE and glyceryl stearate. Preferably 2.2% glyceryl stearate SE and glyceryl stearate. More preferably 1% glyceryl stearate SE and 1.2% glyceryl stearate.

In one embodiment the glyceryl stearate SE employed in the formulation is Surfawax GMS-SE.

In one embodiment the glyceryl stearate employed in the formulation is Surfawax GS.

In one embodiment the lotion comprises glyceryl stearate citrate, such as 1-2.5% glyceryl stearate citrate. Such as 1.1, 1.2, 1.3, 1.4, 1.5, 1.6, 1.7, 1.8, 1.9, 2.0, 2.1, 2.2, 2.3 or 2.4% glyceryl stearate citrate.

Preferably 1% glyceryl stearate citrate.

In one embodiment the gylceryl stearate citrate employed in the formulation is Surfawax C62.

Gelling agent as employed herein is a form of thickener that forms a gel, dissolving in the liquid phase to form a colloid mixture that forms a weakly cohesive internal structure. Suitable gelling agents include, but are not limited to, acacia, alginic acid, bentonite, poly(acrylic acids) carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, xanthan gum and ammonium acryloyldimethyltaurate/VP copolymer. Such as ammonium acryloyldimethyltaurate/VP copolymer.

In one embodiment the lotion comprises gelling agent, such as 0.25-1.25% gelling agent. Such as 0.3, 0.35, 0.4, 0.45, 0.5, 0.55, 0.6, 0.65, 0.7, 0.75, 0.8, 0.85, 0.9, 0.95, 1.0, 1.05, 1.10, 1.15 or 1.20% gelling agent such as ammonium acryloyldimethyltaurate/VP copolymer. Preferably 0.7% ammonium acryloyldimethyltaurate/VP copolymer.

In one embodiment the ammonium acryloyldimethyltaurate/VP copolymer employed in the formulation is Aristoflex AVC.

Corn starch as employed herein is starch from the corn grain obtained from the endosperm of the kernel.

In one embodiment the lotion comprises thickener, such as corn starch. Such as 1-3% corn starch, preferably 2% corn starch.

In one embodiment there is provided a lotion according to the present invention wherein the thickener is corn starch.

In one embodiment there is provided a topical formulation wherein the formulation is a lotion further comprising one or more ingredients independently selected from non-metallic UVA and/or UVB inhibitor such as octocrylene, octinoxate, homosalate or avobenzone or a mixture thereof, $C_{12-15}$ alkyl benzoate, caprylyl methicone, emulsifier such as ceteareth-20 and ceteryl alcohol or glyceryl stearate and PEG-100, gelling agent such as ammonium acrylolydimethyltaurate/VP copolymer, glyceryl monostearate such as glyceryl stearate SE and/or glyceryl stearate, glyceryl stearate citrate, allantoin, caprylic triglyceride, dimethicone, solvent such as 1,3-butylene glycol, mineral oil, pH modifier such as triethanolamine, chelating agent such as edetate disodium, preservative such as phenoxyethanol and ethylhexylglycerine or phenoxyethanol and caprylyl glycol and chlorphenesin and phosphate buffer.

In one embodiment there is provided a lotion consisting essentially of 7-19% non-metallic UVA and/or UVB inhibitor, 54.5-65.5% purified water, 6-15% $C_{12-15}$ alkyl benzoate, 4-8% milk protein fluid, 1-5% caprylyl methicone, 1-2.5% emulsifier, 0.25-1.25% gelling agent, 1-2.5% glyceryl monostearate, 1-2.5% glyceryl stearate citrate, 0.5-1.2% preservative, 0-1% edetate disodium, and 2% thickener.

In one embodiment there is provided a lotion consisting essentially of 10% octocrylene, 3% octinoxate, 3% avobenzone, 58.8% purified water, 8% $C_{12-15}$ alkyl benzoate, 5% LACTOKINE fluid, 4% caprylyl methicone, 1% ceteareth-20 and ceteryl alcohol, 0.7% ammonium acrylolydimethyltaurate/VP copolymer, 1% glyceryl stearate SE, 1.2% glyceryl stearate, 1% glyceryl stearate citrate, 1% phenoxyethanol and ethylhexylglycerine, 0.2% edetate disodium, and 2% corn starch. In one embodiment the viscosity is in the range 25,000 to 130,000 cP, for example 40,000 to 75,000 cP.

In one embodiment the lotion comprises thickener, for example 0.25-0.85% thickener, such as 0.3, 0.35, 0.4, 0.45, 0.5, 0.55, 0.6, 0.65, 0.7, 0.75 or 0.8% thickener, such as acrylates/$C_{10-30}$ alkyl acrylate crosspolymer. Preferably 0.5% acrylates/$C_{10-30}$ alkyl acrylate crosspolymer.

In one embodiment the acrylates/$C_{10-30}$ alkyl acrylate crosspolymer employed in the formulation is Carbopol Ultrez 21 polymer.

In on embodiment the lotion comprises solvent, for example 1-3% solvent, such as 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9% solvent, such as 1,3-butylene glycol. Preferably 2% 1,3-butylene glycol.

In one embodiment the 1,3-butylene glycol is cosmetic grade.

In one embodiment the lotion comprises pH modifier, for example 0.1-3.5% pH modifier, such as 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3 or 3.4% such as triethanolamine. Preferably 0.5% triethanolamine.

In one embodiment the triethanolamine employed in the formulation is Trolamine 99 NF.

In one embodiment the lotion comprises 0.5-2% buffer, such as 0.6, 0.7, 0.8, 0.9, 1.0, 1.1, 1.2, 1.3, 1.4, 1.5, 1.6, 1.7, 1.8 or 1.9% buffer, such as phosphate buffer. Preferably 1% phosphate buffer.

In one embodiment there is provided a lotion consisting essentially of 70-80% purified water, 0.5-2% phosphate buffer, 2-8% milk protein fluid, 0.5-1.5% preservative, 0.1-3.5% triethanolamine, 1-2.5% glyceryl stearate and PEG-100, 1-3% emulsifier, 1-3% dimethicone, 2-6% mineral oil, 2-6% caprylic triglyceride, 0.1-1.5% allantoin, 0-1% edetate disodium, 1-3% 1,3-butylene glycol and 0.25-0.85% thickener.

In one embodiment there is provided a lotion consisting essentially of 75.95% purified water, 1% phosphate buffer, 5% LACTOKINE fluid PF, 1% phenoxyethanol and caprylyl glycol and chlorphenesin, 0.5% triethanolamine, 1.5% glyceryl stearate and PEG-100, 2% cetearyl alcohol and ceteareth-20, 2% dimethicone, 4% mineral oil, 4% caprylic triglyceride, 0.5% allantoin, 0.05% edetate disodium, 2% 1,3-butylene glycol and 0.5% acrylates/$C_{10-30}$ alkyl acrylate crosspolymer. In one embodiment the viscosity is in the range 25,000 to 130,000 cP, for example 30,000 to 50,000 cP.

Generous layer as employed herein means a layer that is intended to sit on the surface of the skin without being rubbed in. Typically the layer is at least 0.5 mm thick, such as 1, 1.5, 2, 2.5, 3, 3.5, 4, 4.5 or 5 mm thick or more.

As often as desired as employed herein means the user may apply the formulation repeatedly with no upper limit on frequency of use.

Relieve discomfort as employed herein means the user experiences a perceptible reduction in symptoms.

In one embodiment the topical formulation has an anti-inflammatory effect. Advantageously this reduces the pain associated with radiation dermatitis.

In one embodiment the milk protein fluid or Lactokine™ has an inhibitory effect on proinflammatory prostaglandin E2.

In one embodiment the topical formulation has an inhibitory effect on proinflammatory prostaglandin E2. In one embodiment PGE2 is reduced to as low as 10% in comparison to non-treated cells. In one embodiment a concentration of 4 mg/ml or more of Lactokine™ is present in the topical formulation to obtain said reduction in PGE2.

In one embodiment the topical formulation protects against a decrease in cell viability. Inflammatory impact is known to reduce cell viability, detectable by MTT assay. In one embodiment 8 mg/ml or more of Lactokine™ in the topical formulation increases cell viability relative to untreated cells. In one embodiment this improvement in cell viability or reduced decrease in cell viability is obtained when the topical formulation is applied either prophylactically or following treatment.

In one embodiment the topical formulation increases the energy level of skin cells. Lactokine™ fluid has been shown to increase ATP level in keratinocytes by up to 30% and in fibroblasts by up to 120%. In one embodiment increasing the energy level of the skin cells aids collagen production.

Fibroblasts are responsible for production of extracellular matrix compounds such as collagen, elastin and fibronectin. LACTOKINE fluid has been shown to stimulate synthesis of collagen type I by up to 40%. Therefore, in one embodiment the topical formulation increases collagen synthesis. In one embodiment increased collagen synthesis protects and treats irradiated skin from breaking down.

In one embodiment damaged cells treated with the topical formulation recover viability more quickly than untreated cells. In one embodiment cell viability is restored more quickly in cells treated with the topical formulation.

In one embodiment the topical formulation reduces skin redness when applied prophylactically or following radiation treatment.

In one embodiment the topical formulation comprises signal and/or messenger molecules, for example cytokines.

In one embodiment the topical formulation has a protective effect when applied prior to radiation treatment. In one embodiment the topical formulation may reduce the amount of damage to DNa caused by radiation therapy.

In one embodiment the hydrogel is cooling.
In one embodiment the hydrogel is anti-inflammatory.
In one embodiment the hydrogel relieves pain.
In one embodiment the lotion hydrates the skin.
In one embodiment the lotion is anti-inflammatory.
In one embodiment the lotion relieves pain.
In one embodiment the lotion inhibits UV.
In one embodiment the formulation is sterilised by gamma irradiation.

The hydrogel represents the first step in a two-step treatment designed to reduce skin discomfort and irritation on patients skin during and post radiation therapy treatments.

The hydrogel is intended for use as soon as possible following treatment. It cools, soothes, hydrates and protects helping to reduce the risk of radiodermatitis through physical means.

The hydrogel should be between body temperature and room temperature when applied. Apply all of the contents of the (6 g) sachet in a generous layer to the affected area. Do not rub into the skin. The gel is most effective when applied in a thick layer and allowed to remain in contact for a minimum of twenty minutes. Any residue may be gently removed, with tepid water and dabbing dry to avoid stressing the treated area.

A critical aspect of the method of the present disclosure is the absorption of heat from the skin by the hydrogel. A further aspect is the soothing of the skin by the milk protein fluid.

Advantageously, because the hydrogel is clear, the area of treatment can be observed through the gel.

In one embodiment the hydrogel is applied to skin, such as the area of radiation treatment, and left for about 10 to 40 minutes, for example 12, 20, 25, 30 or 35 minutes or more. In one embodiment the hydrogel is wiped off the skin surface at the end of this period. In one embodiment the hydrogel is fully absorbed into the skin.

The lotion represents the second step in a two-step treatment designed to reduce skin discomfort and irritation on patients skin during and post radiation therapy treatments.

The lotion moisturises skin without using ingredients that may lead to further damage such as oils, perfumes or metallic particles. In some embodiments the lotion also provides UVA and UVB protection to reduce the risk of reaction to sunlight following treatments.

The lotion should be used at room temperature. Apply the contents of the sachet in generously to the irradiated area a minimum of three times a day and at bedtime. Ensure skin is free of lotion immediately before radiotherapy treatment. Irradiated skin can be irritated by excessive rubbing or abrasion, the lotion should be gently worked into the skin. Use of the lotion should be continued for at least two weeks following radiotherapy course.

A critical aspect of the method of the present disclosure is the continued moisturisation and skin conditioning effect of the lotion. This reduces the effect of any skin damage by helping maintain the integrity of the skin. Where the lotion comprises UVA and/or UVA filters, the lotion also prevents any incidental further damage which may be caused by exposure to UV radiation.

Thus a critical aspect of the method of the present disclosure is the reduction of the loss of skin fluid/moisture and structure by the formulation, particularly the hydrogel formulation. This activity I augmented by the application of the lotion.

In one embodiment the hydrogel is applied once a day.

In one embodiment the lotion is applied to the area of radiation treatment about 1 to 6 hours after radiation exposure, for example 2, 3, 4 or 5 hours, such as 2 to 4 hours after radiation treatment. In one embodiment this is the first application of the lotion following a dose of radiation therapy.

In one embodiment the lotion is applied 1 to 10 times per day, for example 2, 3, 4, 5, 6, 7, 8 or 9 times per day, such as 4 to 6 times or 2 to 3 times per day.

In one embodiment treatment with the formulation relieves pain.

In one embodiment treatment with the formulation reduces burning.

In one embodiment treatment with the formulation reduces itching.

In one embodiment treatment continues for about 3 to 5 weeks following each radiation treatment, such as 4 weeks.

The assessment of radiodermatitis generally utilises a validated assessment tool. The Radiation Therapy Oncology Group (RTOG) and the National Cancer Institute (NCI) have established similar assessment tools that classify radiodermatitis by severity.

In brief, mild radiodermatitis (RTOG and NCI Grade 1) is characterised by mild, blanchable, erythema or dry desquamation. The onset is typically within days to weeks of initiating therapy and symptoms may fade within a month (McQuestion 2006). Dry desquamation may be associated with pruritus, epilation, scaling, and possibly changes in pigmentation. Patients with mild radiodermatitis may report that their skin feels tight (McQuestion 2006).

Moderate radiodermatitis (Grade 2) is often painful and presents as oedema and moist desquamation that is localised to the skin folds (Hymes et al 2006). Bullae may also be present. It is important to note that wet desquamation indicates that the integrity of the dermis is impaired and thus patients are at increased risk for infection with *Staphylococcus aureus* (Hymes et al 2006).

In severe radiodermatitis (Grade 3 and 4), the area of moist desquamation has spread to areas outside of the skin folds.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The present invention is further described by way of illustration only in the following examples:

EXAMPLES

Example 1

21 patients with advanced head and neck cancer undergoing radiochemotherapy and 8 patients with breast cancer undergoing radiotherapy applied the hydrogel and lotion during their course of treatment. The hydrogel was applied once a day within 2 hours of radiation and the lotion was applied four times a day. Clinical response was assessed during and shortly after radiotherapy. Physicians documented their findings on a standardised questionnaire.

TABLE 1 patient characteristics

| Cancer | No. patients | Prophylaxis | Treatment | No. patients with side effects from hydrogel/ lotion | No. patients developing radiation dermatitis |
|---|---|---|---|---|---|
| Head/neck | 21 | 17 | 4 | 0 | 3 |
| breast | 8 | 4 | 4 | 0 | 0 |

Example 2

The hydrogel and lotion were used by 26 patients. Application was uniform: At the beginning of the first symptoms of dermatitis (Erythema), the hydrogel was always applied on the affected area immediately after the radiotherapy, left there for about 20 minutes and then wiped off. The lotion was applied on the same area after 2-4 hours. The following applications of the lotion were individual and their frequency depended on the subjective feelings of each patient.

Of the total number of 26 patients, 15 patients were treated in the head and neck area, 8 patients in the thorax area during radiotherapy of breast cancer, and 3 patients in the pelvic area. Average duration of treatment was 4 weeks. For a majority of cases, the lotion was applied 2-3 times a day.

Twenty-five of 26 patients (96%) reported subjective feelings of relief, reduction of pain, burning or itching.

Example 3

Between November 2010 and January 2011 ten patients with locally advanced head and neck cancer undergoing curative radiotherapy applied the hydrogel and lotion to the irradiated skin during the treatment period. The hydrogel was applied short time after radiation once a day, whereas the lotion was applied four to six times daily. The topical formulations were used during the whole radiation treatment period. Patients were examined, and toxicity was monitored weekly by an experience head and neck oncologist.

Two elderly patients could not manage to follow the instructions and only used the treatments regularly for 2-3 weeks of the treatment period.

The formulations were well tolerated and seemed to be an effective prophylaxis of acute radiation dermatitis. None of the patients developed grade III or IV dermatitis.

REFERENCES

D'haese, S., Bate, T., Claes, S., Boone, A., Vanvoorden, V., & Efficace, F. (2005). Effective management of skin reactions during radiotherapy: A study of nursing practice. *European Journal of Cancer Care,* 14, 28-42.

Fisher J, Scott C, Stevens R, Marconi, B., Champion, L., Freedman, G. M., Asraris, F., Pilepich, M. V., Gagnon, J. D., & Wong, G. (2000). Randomized phase III study comparing best supportive care to Biafine as a prophylactic agent for radiation-induced skin toxicity for women undergoing breast irradiation: Radiation therapy oncology group (RTOG) 97-13. *International Journal of Radiation Oncology, Biology, Physics,* 48, 1307-1310.

Gerlach, M. A. (2005). Wound care issues in the patient with cancer. *Nursing Clinics of North America,* 40, 295-323.

McQuestion, M. (2006). Evidenced-based skin care management in radiation therapy. *Seminars in Oncology Nursing,* 22(3), 163-173.

Hymes, S. R., Strom, E. A., & Fife, C. (2006). Radiation dermatitis: Clinical presentation, pathophysiology, and treatment 2006. *Journal of the American Academy of Dermatology,* 54(1), 28-46.

Porock D, Nikoletti S, Kristjanson L (1999). "Management of radiation skin reactions: literature review and clinical application". *Plast Surg Nurs* 19 (4): 185-92, 223

Pothoff, K., Scharp, M., Fetzner, L., Nejad-Asgari, S., Hafner, M., Klinkner, W., Becker-Schiebe, M., Tonscheidt, H. Schlampp, I., Gilbsse, J. and Debus, J. "First clinical experiences with R1 and R2, a LACTOKINE fluid-based medical device for prophylaxis of radiation dermatitis in cancer patients." Internal data.

Asa Bratland and Henriette Magelssen. "Clinical experience with R1 and R2 lotion for prophylaxis of radiation dermatitis in head and neck cancer patients". Internal data.

David Felti. "Application of R1 gel and R2 lotion in the treatment of radiation dermatitis". Internal data.

Petersen et al "Importance of cell stimulation by cosmetic actives" Olaj, Szappan, Kozmetika (2001)

Paragraphs

1. A topical formulation for the prophylaxis and/or treatment of radiation dermatitis comprising purified water, milk protein fluid and thickener.
2. A topical formulation according to paragraph 1 wherein the viscosity is in the range 25,000 CPS to 510,000 CPS, for example 25,000 CPS to 130,000 CPS or 290,000 CPS to 510,000 CPS.
3. A topical formulation according to any one of paragraphs 1-2 comprising 2-8% milk protein, for example wherein the milk protein fluid is LACTOKINE fluid.
4. A topical formulation according to any one of paragraphs 1-3 further comprising a preservative, for example 0.5-1.5% preservative, such as phenoxyethanol and ethylhexylglycerine or phenoxyethanol and caprylyl glycol and chlorphenesin.
5. A topical formulation according to any one of paragraphs 1-4 further comprising up to 1% chelating agent, such as edetate disodium.
6. A topical formulation according to any one of paragraphs 1-5 wherein the formulation is a hydrogel further comprising one or more ingredients independently selected from:

poly(acrylic acid) such as poly(acrylic acid) 940 and/or poly(acrylic acid) TR1,
pH modifier such as triethanolamine, and
moisturising agent such a glycerine.
7. A hydrogel according to paragraph 6 consisting essentially of:
89-93.5% purified water,
2-8% milk protein fluid,
0.5-1.15% glycerine,
0.1-3.5% triethanolamine,
0.5-1.5% preservative,
0.1-0.9% poly(acrylic acid),
0.25-0.85% thickener, and
0-1% edetate disodium.
8. A hydrogel according to any one of paragraphs 6-7 wherein the thickener is acrylate/$C_{10\text{-}30}$ alkyl acrylate crosspolymer.
9. A hydrogel according to any one of paragraphs 6-8 consisting essentially of:
91.15% purified water,
5% LACTOKINE fluid,
1% glycerine,
0.8% triethanolamine,
0.75% phenoxyethanol and ethylhexylglycerine,
0.4% carbomer 940,
0.3% carbomer TR1,
0.5% acrylate/$C_{10\text{-}30}$ alkyl acrylate crosspolymer, and
0.1% edetate disodium
and wherein the viscosity is in the range 290,000 to 510,000 cP.
10. A hydrogel according to any one of paragraphs 6-9 wherein the hydrogel has high thermal capacity.
11. A topical formulation according to any one of paragraphs 1-4 wherein the formulation is a lotion further comprising one or more ingredients independently selected from:
non-metallic UVA and/or UVB inhibitor such as octocrylene, octinoxate, homosalate or avobenzone or a mixture thereof,
skin conditioning agent such as $C_{12\text{-}15}$ alkyl benzoate, caprylyl methicone, glyceryl monostearate such as glyceryl stearate SE and/or glyceryl stearate, glyceryl stearate citrate, allantoin, caprylic triglyceride or dimethicone,
emulsifier such as ceteareth-20 and ceteryl alcohol or glyceryl stearate and PEG-100,
gelling agent such as ammonium acrylolydimethyltaurate/VP copolymer,
solvent such as 1,3-butylene glycol,
mineral oil,
pH modifier such as triethanolamine,
and
phosphate buffer.
12. A lotion according to paragraph 11 consisting essentially of:
7-19% non-metallic UVA and/or UVB inhibitor,
54.5-65.5% purified water,
6-15% $C_{12\text{-}15}$ alkyl benzoate,
2-8% milk protein fluid,
1-5% caprylyl methicone,
1-2.5% emulsifier,
0.25-1.25% gelling agent,
1-2.5% glyceryl monostearate,
1-2.5% glyceryl stearate citrate,
0.5-1.5% preservative,
0-1% edetate disodium, and
2% thickener.
13. A lotion according to any one of paragraphs 11-12 wherein the non-metallic UVA and/or UVB inhibitors are octocrylene, octinoxate and avobenzone.
14. A lotion according to any one of paragraph 11-13 wherein the thickener is corn starch.
15. A lotion according to any one of paragraphs 11-14 consisting essentially of:
10% octocrylene,
3% octinoxate,
3% avobenzone,
58.8% purified water,
8% $C_{12\text{-}15}$ alkyl benzoate,
5% LACTOKINE fluid,
4% caprylyl methicone,
1% ceteareth-20 and ceteryl alcohol,
0.7% ammonium acrylolydimethyltaurate/VP copolymer,
1% glyceryl stearate SE,
1.2% glyceryl stearate,
1% glyceryl stearate citrate,
1% phenoxyethanol and ethylhexylglycerine,
0.2% edetate disodium, and
2% corn starch
and wherein the viscosity is in the range 25,000 to 130,000 cP.
16. A lotion according to paragraph 11 consisting essentially of:
0.25-0.85% thickener,
1-3% 1,3-butylene glycol,
0-1% edetate disodium,
0.1-1.5% allantoin,
2-6% caprylic triglyceride,
2-6% mineral oil,
1-3% dimethicone,
1-3% emulsifier,
1-2.5% glyceryl stearate and PEG-100,
0.1-3.5% triethanolamine,
0.5-1.5% preservative,
2-8% milk protein fluid,
0.5-2% phosphate buffer solution, and
70-80% purified water.
17. A lotion according to paragraph 11 or 16 wherein the thickener is acrylates/c10-30 alkyl acrylate cross-polymer.
18. A lotion according to any one of paragraphs 11, 16 or 17 wherein the preservative is phenoxyethanol and caprylyl glycol and chlorphenesin.
19. A lotion according to and one of paragraphs 16 to 18 consisting essentially of:
0.5% acrylates/c10-30 alkyl acrylate cross-polymer,
2% 1,3-butylene glycol,
0.05% edetate disodium,
0.5% allantoin,
4% caprylic triglyceride,
4% mineral oil,
2% dimethicone,
2% cetearyl alcohol and ceteareth-20,
1.5% glyceryl stearate and PEG-100,
0.5% triethanolamine,
1% phenoxyethanol and caprylyl glycol and chlorphenesin,
5% LACTOKINE fluid PF,
1% phosphate buffer solution, and
75.95% purified water
and wherein the viscosity is in the range 25,000 to 130,000 cP.

20. A two-step process for the prophylaxis and/or treatment of radiation dermatitis comprising the steps:
   e) applying a generous layer of the hydrogel of any one of paragraphs 6-10 to unbroken skin following radiation therapy and leaving it on the skin for at least 20 minutes;
   f) applying the lotion of any one of paragraphs 11-15 to unbroken skin to provide moisturisation;
   wherein step b) is repeated as often as desired to relieve discomfort.
21. A kit of parts comprising at least one application of the hydrogel formulation of any one of paragraphs 6-10 and at least one application of the lotion formulation of any one of paragraphs 11-19.
22. A method of prophylaxis and/or treatment for radiation dermatitis comprising administering to patient in need thereof the hydrogel of any one of paragraphs 6-10 and/or the lotion of any one of paragraphs 11-19.

The invention claimed is:

1. A process for addressing radiation dermatitis comprising the steps of:
   a) applying a layer of hydrogel to unbroken skin following radiation therapy and leaving the hydrogel thereon for at least 20 minutes; and
   b) applying lotion to the unbroken skin to provide moisturisation;
   wherein step b) is repeated as often as desired to relieve discomfort;
   wherein the hydrogel is a topical formulation comprising purified water, milk protein fluid and thickener, and one or more ingredients selected from: a polyacrylic acid, pH modifier, and moisturising agent;
   wherein the lotion is a topical formulation comprising purified water, milk protein fluid and thickener, and one or more ingredients selected from: non-metallic UVA inhibitor, non-metallic UVB inhibitor, a skin conditioning agent, emulsifier, gelling agent, solvent, mineral oil, pH modifier and phosphate buffer; and
   wherein the lotion consists essentially of:
   7-19% weight/weight (w/w) non-metallic UVA or UVB inhibitor,
   54.5-65.5% w/w purified water,
   6-15% w/w C 12-15 alkyl benzoate,
   4-8% w/w milk protein fluid,
   1-5% w/w caprylyl methicone,
   1-2.5% w/w emulsifier,
   0.25-1.25% w/w gelling agent,
   1-2.5% w/w glyceryl monostearate,
   1-2.5% w/w glyceryl stearate citrate,
   0.5-1.2% w/w preservative,
   0-1% w/w edetate disodium, and
   2% w/w thickener.

2. The process according to claim 1, wherein the hydrogel is applied after radiation therapy to a part of the skin that has received radiation therapy, and the lotion is applied after the hydrogel within about 1 to 6 hours after radiation therapy to the same part of the skin that has received the radiation therapy.

3. The process according to claim 2, wherein when radiation therapy is applied in a daily dose, the hydrogel is applied once after each daily dose of radiation therapy and the lotion is applied 1 to 10 times per day.

4. The process according to claim 3, wherein the lotion is applied 2 to 6 times per day.

5. The process according to claim 1, wherein the hydrogel is wiped off the skin or absorbed into the skin before application of the lotion.

6. The process according to claim 1, wherein the process is repeated daily for 3 to 5 weeks, following radiation treatment.

7. The process according to claim 1, wherein,
   in the hydrogel, the pH modifier comprises triethanolamine; and
   the moisturising agent is selected from the group consisting of glycerine, sorbitol, polyethylene glycols, urea, and propylene glycol.

8. The process according to claim 1, wherein a viscosity of the lotion is in the range of 25,000 CPS to 130,000 CPS and a viscosity of the hydrogel is in the range of 290,000 cP to 510,000 cP.

9. The process according to claim 1, wherein the hydrogel comprises 4-8% w/w milk protein fluid.

10. The process according to claim 1, wherein the hydrogel and/or the lotion further comprises a preservative selected from phenoxyethanol and ethylhexylglycerine.

11. The process according to claim 1, wherein the hydrogel comprises up to 1% w/w chelating agent.

12. The process according to claim 1, wherein the hydrogel consists essentially of:
   89-93.5% w/w purified water,
   4-8% w/w milk protein fluid,
   0.5-1.15% w/w glycerine,
   0.1-3.5% w/w triethanolamine,
   0.5-1.2% w/w preservative,
   0.1-0.9% w/w polyacrylic acid),
   0.25-0.85% w/w thickener, and
   0-1% w/w edetate disodium.

13. The process according to claim 12, wherein the thickener is acrylate/C 10-30 alkyl acrylate crosspolymer.

14. The process according to claim 1, wherein the hydrogel consists essentially of:
   91.15% w/w purified water,
   5% w/w milk protein fluid,
   1% w/w glycerine,
   0.8% w/w triethanolamine,
   0.75% w/w phenoxyethanol and ethylhexylglycerine,
   0.7% w/w polyacrylic acid,
   0.5% w/w acrylate/C 10-30 alkyl acrylate crosspolymer, and
   0.1% w/w edetate disodium and wherein a viscosity of the hydrogel is in the range 290,000 to 510,000 cP.

15. The process according to claim 1, wherein the lotion consists essentially of
   10% w/w octocrylene,
   3% w/w octinoxate,
   3% w/w avobenzone,
   58.8% w/w purified water,
   8% w/w C 12-15 alkyl benzoate,
   5% w/w milk protein fluid,
   4% w/w caprylyl methicone,
   1% w/w ceteareth-20 and ceteryl alcohol,
   0.7% w/w ammonium acrylolydimethyltaurate/vinyl pyrrolidone copolymer,
   1% w/w glyceryl stearate self-emulsifying,
   1.2% w/w glyceryl stearate,
   1% w/w glyceryl stearate citrate,
   1% w/w phenoxyethanol and ethylhexylglycerine,
   0.2% w/w edetate disodium, and
   2% w/w corn starch
   and wherein a viscosity of the lotion is in the range of 25,000 to 130,000 cP.

16. A process for addressing radiation dermatitis comprising the steps of:
  a) applying a layer of hydrogel to unbroken skin following radiation therapy and leaving the hydrogel on the skin for at least 20 minutes; and
  b) applying a lotion to the unbroken skin to provide moisturisation;
wherein step b) is repeated as often as desired to relieve discomfort;
  wherein the hydrogel is a topical formulation comprising purified water, milk protein fluid and thickener, a polyacrylic acid, a pH modifier comprising trolamine, and a moisturising agent comprising a glycerine;
  wherein the lotion is a topical formulation comprising purified water, milk protein fluid and thickener, non-metallic UVA or non-metallic UVB inhibitor, a skin conditioning agent, emulsifier, gelling agent, solvent, mineral oil, pH modifier and phosphate buffer and
  wherein the lotion consists essentially of:
7-19% weight/weight (w/w) non-metallic UVA or UVB inhibitor,
54.5-65.5% w/w purified water,
6-15% w/w C 12-15 alkyl benzoate,
4-8% w/w milk protein fluid,
1-5% w/w caprylyl methicone,
1-2.5% w/w emulsifier,
0.25-1.25% w/w gelling agent,
1-2.5% w/w glyceryl monostearate,
1-2.5% w/w glyceryl stearate citrate,
0.5-1.2% w/w preservative,
0-1% w/w edetate disodium, and
2% w/w thickener.

17. A process for addressing radiation dermatitis comprising the steps of:
  a) applying a layer of hydrogel to unbroken skin following radiation therapy and leaving the hydrogel on the skin for at least 20 minutes; and
  b) applying a lotion to unbroken skin to provide moisturisation;
  wherein step b) is repeated as often as desired to relieve discomfort;
wherein when radiation therapy is applied in a daily dose, the hydrogel is applied once after each daily dose of radiation therapy and the lotion is applied 1 to 10 times per day;
  wherein the hydrogel is a topical formulation comprising purified water, milk protein fluid and thickener and the hydrogel has a viscosity is in the range 290,000 to 510,000 cP;
  wherein the lotion is a topical formulation comprising purified water, milk protein fluid and thickener, the lotion having a viscosity is in the range 25,000 to 130,000 cP; and
  wherein the lotion consists essentially of:
7-19% w/w non-metallic UVA or UVB inhibitor,
54.5-65.5% w/w purified water,
6-15% w/w C 12-15 alkyl benzoate,
4-8% w/w milk protein fluid,
1-5% w/w caprylyl methicone,
1-2.5% w/w emulsifier,
0.25-1.25% w/w gelling agent,
1-2.5% w/w glyceryl monostearate,
1-2.5% w/w glyceryl stearate citrate,
0.5-1.2% w/w preservative,
0-1% w/w edetate disodium, and
2% w/w thickener.

\* \* \* \* \*